(12) United States Patent
Muldoon et al.

(10) Patent No.: US 10,147,970 B2
(45) Date of Patent: Dec. 4, 2018

(54) CHLORIDE-FREE ELECTROLYTE FOR A MAGNESIUM BATTERY AND A METHOD TO CONVERT A MAGNESIUM ELECTROLYTE TO A CHLORIDE-FREE ELECTROLYTE

(71) Applicant: Toyota Motor Engineering & Manufacturing North America, Inc., Erlanger, KY (US)

(72) Inventors: John G. Muldoon, Saline, MI (US); Claudiu B. Bucur, Ypsilanti, MI (US)

(73) Assignee: Toyota Motor Engineering & Manufacturing North America, Inc., Erlanger, KY (US)

( * ) Notice: Subject to any disclaimer, the term of this patent is extended or adjusted under 35 U.S.C. 154(b) by 771 days.

(21) Appl. No.: 14/263,392

(22) Filed: Apr. 28, 2014

(65) Prior Publication Data
US 2015/0311565 A1    Oct. 29, 2015

(51) Int. Cl.
*C07F 5/02* (2006.01)
*H01M 4/134* (2010.01)
(Continued)

(52) U.S. Cl.
CPC ......... *H01M 10/0569* (2013.01); *C07F 5/027* (2013.01); *H01M 4/134* (2013.01); *H01M 4/38* (2013.01); *H01M 4/466* (2013.01); *H01M 4/483* (2013.01); *H01M 4/502* (2013.01); *H01M 4/54* (2013.01); *H01M 4/58* (2013.01); *H01M 10/054* (2013.01); *H01M 10/0568* (2013.01);
(Continued)

(58) Field of Classification Search
None
See application file for complete search history.

(56) References Cited

U.S. PATENT DOCUMENTS 4,139,681 A * 2/1979 Klemann ............. H01M 10/36
429/199
4,808,282 A * 2/1989 Gregory ................. C07F 5/027
205/420

(Continued)

FOREIGN PATENT DOCUMENTS

CN       101210026 A  *  7/2008
CN       103193813 A  *  7/2013
WO    WO 2014168671 A1 * 10/2014   ........ H01M 10/0568

OTHER PUBLICATIONS

Connor et al., Electrodeposition of Metals from Organic Solutions, J. Electrochem. Soc. 1957 vol. 104, issue 1, 38-41, doi: 10.1149/1.2428492, 4 pages total.*

(Continued)

*Primary Examiner* — Ula C Ruddock
*Assistant Examiner* — Anna Korovina
(74) *Attorney, Agent, or Firm* — Oblon, McClelland, Maier & Neustadt, L.L.P.

(57) ABSTRACT

A method to prepare a chloride free magnesium electrolyte salt is provided. According to the method a water stable borate or carborate anion is converted to metal salt of an alkali metal or silver by an ion exchange and then converted to a chloride free magnesium salt by another ion exchange. A chloride free magnesium salt suitable as an electrolyte for a magnesium battery and a magnesium battery containing the chloride free magnesium electrolyte are also provided.

21 Claims, 2 Drawing Sheets

(51) Int. Cl.
  *H01M 4/38* (2006.01)
  *H01M 4/48* (2010.01)
  *H01M 4/50* (2010.01)
  *H01M 4/54* (2006.01)
  *H01M 4/58* (2010.01)
  *H01M 10/054* (2010.01)
  *H01M 10/0568* (2010.01)
  *H01M 4/46* (2006.01)
  *H01M 10/0569* (2010.01)

(52) U.S. Cl.
  CPC ............... *H01M 2300/0028* (2013.01); *H01M 2300/0037* (2013.01)

(56) References Cited

U.S. PATENT DOCUMENTS

| | | | | |
|---|---|---|---|---|
| 6,162,950 | A * | 12/2000 | Lee | C07F 5/027 568/1 |
| 8,318,354 | B2 | 11/2012 | Muldoon et al. | |
| 2001/0014739 | A1 * | 8/2001 | Mitsui | C07F 5/027 546/13 |
| 2004/0137324 | A1 | 7/2004 | Itaya et al. | |
| 2013/0034780 | A1 * | 2/2013 | Muldoon | H01M 4/661 429/339 |
| 2013/0266851 | A1 | 10/2013 | Singh et al. | |
| 2013/0337328 | A1 | 12/2013 | Yamamoto et al. | |
| 2014/0349178 | A1 * | 11/2014 | Mohtadi | H01M 10/0568 429/200 |
| 2014/0349199 | A1 * | 11/2014 | Mohtadi | H01M 4/381 429/337 |

OTHER PUBLICATIONS

Carter et al., Boron Clusters as Highly Stable Magnesium-Battery Electrolytes, Angew. Chem. 2014, 126, 3237-3241, DOI: 10.1002/ange.201310317, 5 pages total.*

Lee et al., The Synthesis of a New Family of Boron-Based Anion Receptors and the Study of Their Effect on Ion Pair Dissociation and Conductivily of Lithium Salts in Nonaqueous Solutions, J. Electrochem. Soc. 1998 145(8): 2813-2818; doi:10.1149/1.1838719, 6 pages total.*

Guo et al., Boron-based electrolyte solutions with wide electrochemical windows for rechargeable magnesium batteries, Energy Environ. Sci., 2012, 5, 9100, DOI: 10.1039/c2ee22509c, 7 pages total.*

Popovych, International Union of Pure and Applied Chemistry, Analytical Chemistry Division Commission on Solubility Data, Solubility Data Series, vol. 18, Tetraphenylborates, 1981, 261 pages total.*

Jolicoeur et al., Cider Workshop, Potassium carbonate/bicarbonate, 2011, 2 pages total.*

D'Aprano et al., Precipitation of Slightly Soluble Silver Salts in Reversed AOT Micelles: Calorimetric Investigation, Journal of Solution Chemistry, vol. 20, No. 3, 1991, 6 pages total.*

Zhang, CN101210026, Machine Translation, 13 pages total.*

Shubin, CN103193813, Machine translation, 31 pages total.*

Muldoon et al., Corrosion of magnesium electrolytes: chlorides—the culprit, Energy Environ. Sci., 2013, 6, 482, DOI: 10.1039/c2ee23686a; 6 pages total.*

Nishida et al., "Tetrakis[3,5-bis(trifluoromethyl)phenyl]borate. Highly Lipophilic Stable Anionic Agent for Solvent-extraction of Cations", Bull. Chem. Soc. Jpn., 1984, 57, 2600-2604; 5 pages total.*

Yakelis et al., "Safe Preparation and Purification of Sodium Tetrakis[(3,5-trifluoromethyl)phenyl]borate (NaBArF24): Reliable and Sensitive Analysis of Water in Solutions of Fluorinated Tetraarylborates", Organometallics, 2005, 24, 3579-3581, DOI: 10.1021/om0501428; 3 pages total.*

Kotani et al., "Electrolyte roadblocks to a magnesium rechargeable battery", Energy Environ. Sci., 2012, 5, 5941, DOI: 10.1039/c2ee03029b; 11 pages total.*

Hwang et al. ("Magnesium Borohydride: From Hydrogen Storage to Magnesium Battery", Angew. Chem. Int. Ed. 2012, 51, 9780-9783, DOI: 10.1002/anie.201204913, 4 pages total.*

Wayne E. Buschmann, et al., "Sources of Naked Divalent First-Row Metal Ions: Synthesis and Characterization of $[M^{II}(NCMe)_6]^{2+}$ (M=V, Cr, Mn, Fe, Co, Ni) Salts of Tetrakis[3,5-bis(trifluoromethyl)phenyl]borate" Chem. Eur. J. 1998, 4, No. 9, (pp. 1731-1737).

Notification of the First Office Action dated Sep. 5, 2018 in connection with Chinese Patent Application No. 201510211870.8 filed Apr. 27, 2015 with English translation.

Reid et al, "Electrodeposition of Metals from Organic Solutions", J. Electrochem. Soc. 104(1):3841 (1957).

* cited by examiner

CHLORIDE-FREE ELECTROLYTE FOR A MAGNESIUM BATTERY AND A METHOD TO CONVERT A MAGNESIUM ELECTROLYTE TO A CHLORIDE-FREE ELECTROLYTE

BACKGROUND OF THE INVENTION

Field of the Invention

The present invention is directed to a method to prepare a chloride-free magnesium electrolyte and a magnesium electrolyte containing the chloride-free active material.

Discussion of the Background

Magnesium batteries have been the subject of high interest and significant research and development effort in order to provide more economical, safer and higher capacity batteries to displace or supplement the conventional lithium batteries. Compared to lithium Mg potentially has a volumetric capacity of 3832 mAh cm$^{-3}$ which is significantly greater than the 2062 mAh cm$^{-3}$ of Li. Additionally, Mg has a negative reduction potential of −2.356V vs NHE. As the seventh most abundant element in the earth's crust, Mg has a lower resource cost and a lower environmental impact profile (see Aurbach: Nature, Vol 407, pp 724-727, 2000).

Significantly, Mg does not suffer from dendrite formation, which renders Li metal unsafe for commercialization as a high capacity anode material (West: Journal of Electrochemical Communications, Vol 155, pp A806-A811, 2008).

An ongoing objective in battery research is increasing the energy density beyond that offered by lithium ion batteries. This may require a shift towards batteries containing a pure metal anode. However, in the case of lithium, deposition occurs unevenly with formation of dendrites which leads to safety concerns during cycling. In contrast to lithium metal, magnesium metal deposition is not plagued by dendritic formation. Additionally, magnesium is more stable than lithium when exposed to air. However, magnesium has a reductive potential of −2.36 V vs. NHE and has a unique electrochemistry which precludes the use of magnesium electrolytes that are analogues of lithium electrolytes. Reduction of magnesium analogues such as $Mg(PF_6)_2$, $Mg(ClO_4)_2$ and $Mg(TFSI)_2$ results in the formation of a blocking film on the magnesium anode surface through which successful deposition of magnesium has not been observed. (Feng, Z: Surface Coating Technologies, Vol 201, pp 3783-3787, 2006).

Reports of effective magnesium electrodeposition from Grignard reagents in ethereal solutions date as far back as 1927 and have periodically appeared in the literature ever since. In an attempt to enhance the stability of the electroplating baths based on Grignards, in 1957 Connor et al. investigated the electrodeposition of magnesium from magnesium borohydride $Mg(BH_4)_2$ generated in situ by the reaction of $MgBr_2$ and $LiBH_4$. Unfortunately, boron and magnesium co-deposit in a 1:9 ratio. Recently, Mohtadi et al. have demonstrated the use of magnesium borohydride as an electrolyte for magnesium battery. The oxidative stability of $Mg(BH_4)_2$ has been reported similar to Grignard solutions. However, one of the obstacles in developing high voltage rechargeable magnesium batteries is moving beyond the oxidative stability of Grignards such as ethylmagnesium bromide (EtMgBr) and butylmagnesium chloride (BuMgCl) which have an oxidative stability of 1.3V vs. Mg. The low oxidative stability of Grignard solutions limits the choice of available cathodes. In 1990, Gregory et al. synthesized an electrolyte $Mg(B(C_4H_9)_4)_2$ from the reaction of dibutylmagnesium and the Lewis acid tri-n-butylborane which showed enhanced oxidative stability versus BuMgBr. It was assumed that the character of the Lewis acid could be a factor in improving the voltage stability. Gregory also evaluated magnesium deposit quality by spiking of alkyl Grignards such as ethylmagnesium chloride (EtMgCl) and methylmagnesium chloride (MeMgCl) with aluminum trichloride ($AlCl_3$) to enhance electrochemical plating.

Aurbach et al has popularized a novel class of electrolytes called magnesium organohaloaluminates. One such electrolyte called APC is generated in situ by the reaction of aluminum trichloride ($AlCl_3$) with the Grignard phenylmagnesium chloride (PhMgCl) in a 1:2 ratio and has an oxidative stability in excess of 3.2 V vs. Mg and can deposit/dissolve magnesium with high coulombic efficiencies. All crystallized magnesium organohaloaluminates share the general cation $(Mg_2(\mu\text{-}Cl)_3 \cdot 6THF)+$ and their redox stability is determined by their unique anions. Magnesium organohaloaluminate electrolytes possess a high oxidative stability on inert electrodes (above 3.0 V vs. Mg) such as Pt or glassy carbon and are capable of depositing and stripping magnesium at high currents. However, they have been reported to be corrosive towards less noble metals such as aluminum, nickel and stainless steel which limits charging in a coin cell battery configuration to under 2.2 V due to the utilization of such metals in the casing and current collector material. Since the oxidative stability of electrolytes governs the choice of cathodes it is of paramount importance to develop a non-corrosive magnesium electrolyte which will permit discovery of high voltage cathodes. Improving the voltage stability of magnesium electrolytes on stainless steel is crucial because stainless steel is a widely used current collector and a major component in a variety of batteries such as coin cells. Current state of the art magnesium organohaloaluminate electrolytes limit the usage of Mg battery coin cells to operating under 2.3V vs Mg. It has been well established that chloride ions are some of the most severe corroding ions which attack metal surfaces non-uniformly with the formation of pits. However, previous to this invention no report identifying the problem of chloride ion content of a magnesium electrolyte and describing effort to prepare a chloride-free magnesium electrolyte has been found.

Yamamoto et al. (U.S. 2013/0337328) describes a magnesium electrochemical cell containing a magnesium metal or metal alloy as a negative electrode, a graphite fluoride/copper positive electrode and an electrolyte which is a mixture of complexed magnesium metal ions in an ether solvent (1,2 dimethoxyethane), an alkyl trifluoromethanesulfonate, a quaternary ammonium salt and/or a methylimidazolium salt. The mixture also contains an aluminum halide ($AlCl_3$) and after dissolving the magnesium and aluminum halide an ether complex of boron trifluoride is added. A range of boron salts are described as possible components. However, nowhere does this reference identify a problem due to chloride content of the electrolyte or disclose or suggest preparation of a chloride free magnesium complex salt as an electrolyte.

The present inventors (U.S. 2013/0034780) (U.S. Pat. No. 8,318,354) described the synthesis and structural identification of magnesium complex salts which may be the basic starting material for the present invention. However, conversion to a chloride free complex was not disclosed or suggested.

Singh et al. (U.S. 2013/0266851) describes a magnesium electrochemical cell having a negative electrode containing tin as an active component. Conventionally known electrolytes such as Grignard based systems and magnesium bis(trifluoromethanesulfonyl)imide are employed. However, nowhere does this reference identify a problem due to chloride content of the electrolyte or disclose or suggest preparation of a chloride free magnesium complex salt as an electrolyte.

Itaya et al. (U.S. 2004/0137324) describes an electrolyte for a magnesium battery that is composed of magnesium bistrifluoromethanesulfonimide in a nonaqueous organic solvent such as a carbonate, an ether or a molten salt. However, nowhere does this reference identify a problem due to chloride content of the electrolyte or disclose or suggest preparation of a chloride free magnesium complex salt as an electrolyte.

It was the inventors' initial hypothesis that one possible cause for the corrosive character of magnesium organohaloaluminate electrolytes is the presence of chlorides in the cation $(Mg_2(\mu\text{-}Cl)_3 \cdot 6THF)^+$ of the magnesium salt. It was therefore an object of the present invention to discover a method to prepare chloride-free magnesium electrolytes which are compatible with non-noble metals such as Al, Cu and stainless steel for utility in a magnesium battery.

It was a further object to prepare chloride-free electrolytes for a magnesium battery.

It was a further object to provide magnesium electrochemical cells employing the chloride-free magnesium electrolyte and magnesium batteries containing the electrochemical cell.

SUMMARY OF THE INVENTION

These and other objects have been achieved by the present invention, the first embodiment of which includes a method to prepare a magnesium salt of formula (I):

wherein Solvent is a nonaqueous solvent comprising an ether oxygen and y is an integer of 2 to 6, and A is at least one of a water stable borate anion or carborate anion. The method comprises at least one ion exchange operation of $Mg^{2+}$ for a metal ion $M^+$ in the nonaqueous solvent (Solvent) according to the equation (c):

$$2(A^-M^+) + MgBr_2 \rightarrow A_2Mg(Solvent)_y + 2MBr(s) \quad (c)$$

wherein $M^+$ is at least one selected from the group consisting of $Li^+$, $Na^+$, $K^+$ $Rb^+$, $Cs^+$ and $Ag^+$.

In selected embodiments of the present invention the metal M may be potassium (K) or silver (Ag) and in one further embodiment of the method a double exchange where KA is first prepared and then the KA is converted by ion exchange to AgA which, in turn, is converted to the magnesium electrolyte according to equation (c).

In a specific embodiment, the anion A is the borate anion of formula (II):

wherein the R groups are each independently an alkyl group of 1-6 carbon atoms, optionally substituted with F, an aryl group optionally substituted with F, and an alkylphenyl group optionally substituted with F.

In particular embodiments the borate anion of formula (II) is an anion of formula (IV):

wherein each Ph group is independently an aryl group optionally substituted with F, and an alkylphenyl group optionally substituted with F.

In another embodiment, the anion A is a carborate anion of formula (III):

wherein the carborate is an anion of an ortho-carborane, meta-carborane or para-carborane.

In a further embodiment, the present invention includes a magnesium electrolyte of formula (I):

wherein Solvent is a nonaqueous solvent comprising an ether oxygen and y is an integer of 2 to 6, A is at least one of a water stable borate anion or carborate anion, and the magnesium electrolyte salt is free of chlorides.

In special embodiments the electrolyte contains the borate anion of formula (V) and/or the borate anion of formula (VI) as anion A:

wherein Mes is a 3,5-dimethylphenyl group.

The present invention also includes a magnesium battery, comprising: a negative electrode comprising magnesium; a positive electrode; a solvent; and a magnesium electrolyte of formula (I):

wherein Solvent of formula (I) is a nonaqueous solvent comprising an ether oxygen and y is an integer of 2 to 6, A is at least one of a water stable and air stable borate anion or carborate anion, and the magnesium electrolyte is free of chlorides.

The forgoing description is intended to provide a general introduction and summary of the present invention and is not intended to be limiting in its disclosure unless otherwise explicitly stated. The presently preferred embodiments, together with further advantages, will be best understood by reference to the following detailed description taken in conjunction with the accompanying drawings.

DETAILED DESCRIPTION OF THE INVENTION

Within the description of this invention, all cited references, patents, applications, publications and articles that are under authorship, joint authorship or ascribed to members of the Assignee organization are incorporated herein by reference. Where a numerical limit or range is stated, the endpoints are included. Also, all values and subranges within a numerical limit or range are specifically included as if explicitly written out. As used herein, the words "a" and "an" and the like carry the meaning of "one or more." The phrases "selected from the group consisting of," "chosen from," and the like include mixtures of the specified materials. Terms such as "contain(s)" and the like are open terms meaning 'including at least' unless otherwise specifically noted.

As described above, the present inventors in the course of investigating electrolyte systems suitable especially for magnesium electrochemical cells and/or reversible magnesium batteries have recognized that a basic component of specific electrolytes of interest is the magnesium dimer of the formula:

$$(Mg_2(\mu\text{-Cl})_3 \cdot 6THF)^+.$$

The redox stability of the specific electrolyte is determined by the associated anion. Magnesium organohaloaluminate electrolytes possess a high oxidative stability on inert electrodes (above 3.0 V vs. Mg) such as Pt or glassy carbon and are capable of depositing and stripping magnesium at high currents. However, they have been reported to be corrosive towards less noble metals such as aluminum, nickel and stainless steel which limits charging in a coin cell battery configuration to under 2.2 V due to the utilization of such metals in the casing and current collector material. Since the oxidative stability of electrolytes governs the choice of cathodes, development of a non-corrosive magnesium electrolyte to couple with a high voltage cathode is necessary for the development of efficient magnesium batteries of higher capacity and stability that are economically attractive. Such economically attractive batteries will employ metals such as aluminum, copper and stainless steel, all of which suffer corrosion and pitting in the presence of chloride ions.

To address this problem the present invention provides a method to prepare a chloride-free magnesium electrolyte wherein a magnesium ion is "naked" in the sense that it is coordinated by solvent molecules and not complexed with chlorides as shown in the complex dimer conventionally formed in organohaloaluminate electrolytes.

Thus, in a first embodiment, the present invention provides a method to prepare a magnesium salt of formula (I):

$$[A]_2Mg(Solvent)_y \quad (I)$$

wherein Solvent is a nonaqueous solvent comprising an ether oxygen, y is an integer of 2 to 6, and A is at least one of an air stable and water stable borate anion or carborate anion. The method comprises at least one ion exchange operation of $Mg^{2+}$ for a metal ion $M^+$ in the nonaqueous solvent (Solvent) according to the equation (c):

$$2(A^-M^+) + MgBr_2 \rightarrow A_2Mg(Solvent)_y + 2MBr(s) \quad (c)$$

wherein $M^+$ is at least one selected from the group consisting of $Li^+$, $Na^+$, $K^+$ $Rb^+$, $Cs^+$ and $Ag^+$.

The overall effect of the process of the present invention is to convert the salt of the magnesium dimer $[(Mg_2(\mu\text{-Cl})_3 \cdot 6THF)^+][A]$ to a non-dimer magnesium cation that is free of coordination with chloride ions.

The anion $A^-$ that is an air stable and water stable borate or corborate may be obtained by reaction of a Grignard reagent with an appropriate trisubstituted boron Lewis acid or with a carborane. In either case, a reaction mixture containing a complex salt of the anion with $(Mg_2(\mu\text{-Cl})_3 \cdot 6THF)^+$ is obtained. The complex salt may be separated and isolated from the mixture. Subsequently, via an aqueous ion exchange reaction $A^-$ may be converted to a salt of a metal (M) ion wherein M is at least one selected from the group consisting of Li, Na, K, Rb, Cs and Ag. The ion exchange may be described by the equation:

$$[Mg_2(\mu\text{-Cl})_3 \cdot 6THF]^+A^- + M_2CO_3, MHCO_3 \rightarrow MA + [Mg_2(\mu\text{-Cl})_3 \cdot 6THF]^+$$

Because the ion exchange is conducted in an aqueous medium, one of ordinary skill will recognize that the described ion exchange may only be effective so long as the anion $A^-$ is stable to decomposition or degradation in the aqueous ion exchange medium.

According to one embodiment M is K and the ion exchange is described by equation (a):

$$[Mg_2(\mu\text{-Cl})_3 \cdot 6THF]^+A^- + K_2CO_3, KHCO_3 \rightarrow KA + [Mg_2(\mu\text{-Cl})_3 \cdot 6THF]^+ \quad (a)$$

According to another embodiment, M is Ag and an equation analogous to (a) may be written to describe the ion exchange.

The anion $A^-$ may be a borate anion of formula (II):

$$(BR_4)^- \quad (II)$$

wherein the R groups are each independently an alkyl group of 1-6 carbon atoms, optionally substituted with F, an aryl group optionally substituted with F, and an alkylphenyl group optionally substituted with F.

According to embodiments of the present invention the borate anion of formula (II) is an anion of formula (IV):

$$[BPh_4]^- \quad (IV)$$

wherein each Ph group is independently an aryl group optionally substituted with F, and an alkylphenyl group optionally substituted with F. Explicit anions of this embodiment include an anion of formula (V):

$$[(C_6F_5)_3B(C_6H_5)]^- \quad (V); or$$

an anion of formula (VI):

$$[(MeS)_3B(C_6H_5)]^- \quad (VI)$$

wherein Mes is a 3,5-dimethylphenyl group.

Upon completion of the ion exchange to form MA, the MA may be extracted from the ion exchange reaction medium by ether extraction. The MA dissolves in the ether and the ether extract may be separated from the aqueous phase and the ether evaporated under reduced pressure to obtain the MA salt as a solid.

According to the method of the present invention, the MA obtained from the ether extract may be converted to a $A_2Mg(Solvent)_y$ electrolyte salt directly as described in the following paragraphs or in the circumstance that the MA salt is a salt wherein M is $Li^+$, $Na^+$, $K^+$ $Rb^+$ or $Cs^+$, the salt may be further reacted in a second ion exchange reaction in acetonitrile according to the following equation:

$$MA + AgNO_3 \rightarrow AgA + MNO_3(s).$$

In a preferred embodiment the potassium salt (KA) is first prepared in an aqueous ion exchange as described above and obtained from an ether extract as described. Then the KA may be converted to the Ag salt via ion exchange in acetonitrile according to the following equation:

$$KA + AgNO_3 \rightarrow AgA + KNO_3(s).$$

This exchange is facilitated because the AgA salt is soluble in the acetonitrile while potassium nitrate precipitates as a solid.

Alternatively, the MA salt may be converted to the magnesium salt by ion exchange reaction of 2 equivalents of MA with 1 equivalent of magnesium bromide in a nonaqueous ether solvent according to equation (c):

$$2(A^-M^+) + MgBr_2 \rightarrow A_2Mg(Solvent)_y + 2MBr(s) \quad (c)$$

The nonaqueous ether solvent is any solvent containing an ether oxygen and includes, for example, tetrahydrofuran (THF), dimethoxyethane (DME) and diethylene glycol dimethyl ether (diglyme) (DGM). These examples are not intended to be limiting and any monodentate, bidentae or tridentate ether may be suitable as long as other groups reactive to the anion A⁻ are not present. Tetrahydrofuran may be a preferred ether solvent for conducting the ion exchange of equation (c). Exemplary examples of equation (c) conducted in THF are indicated by the following equations:

formula (VII)

formula (VIII)

Precipitation of the AgBr is indicative of the occurrence of the exchange reaction. Crystals of the chloride-free magnesium electrolyte salt may be obtained from the ether solvent by layering with a hydrocarbon solvent such as hexane, cyclohexane or a petroleum ether. The obtained crystals may be crystallized from an aromatic solvent such as toluene or xylene.

In another embodiment, the present invention provides chloride-free magnesium electrolyte salts that are obtained by the ion exchange methods described above. The method described may be universally employed to prepare magnesium salts which are chloride free and which are described as "naked" in this respect. As indicated in the description of the Example, the magnesium is coordinated by solvent molecules. When the solvent is THF, a monodentate ligand, a total of six molecules may be present. However, if the salt is crystallized from a solvent such as toluene, toluene may partially replace THF in the solvent sphere about the magnesium ion.

In further embodiments, the present invention provides a magnesium battery, comprising:
a negative electrode comprising magnesium;
a positive electrode;
a solvent; and
an electrolyte salt of formula (I):

(I)

wherein

Solvent is a nonaqueous solvent comprising an ether oxygen and y is an integer of 2 to 6.

In a further embodiment of the invention, the magnesium battery contains at least one stainless steel component and in a preferred embodiment the current collector for the magnesium battery is stainless steel.

This electrolyte of formula (I) is soluble in ether solvents such as tetrahydrofuran, polyethers, 2-methyl tetrahydrofuran, dimethoxyethane, dimethyl glycol, glyme, monoglyme, ethylene glycol, dimethyl ether, diethyl ether, ethyl glyme, diglyme, proglyme, ethyl diglyme, triglyme, butyl diglyme, tetraglyme, polyglyme, higlyme or combinations thereof. One may also dissolve this salt [A]₂Mg(Solvent)ᵧ in an ether containing solvent and soak it in a polymer film to form a polymer based electrolyte.

The positive electrode of the Mg battery may contain any positive electrode active material which is stable to the Mg electrolyte of formula (I). Examples of such positive electrode active material may include sulfur, Chevrel phase Mo₆S₈, MnO₂, CuS, Cu₂S, Ag₂S, CrS₂, VOPO₄, layered structure compounds such as TiS₂, V₂O₅, MgVO₃, MoS₂, MgV₂O₅, MoO₃, Spinel structured compounds such as CuCr₂S₄, MgCr₂S₄, MgMn₂O₄, Mg₂MnO₄, NASICON structured compounds such as MgFe₂ (PO₄)₃ and MgV₂ (PO₄)₃, Olivine structured compounds such as MgMnSiO₄ and MgFe₂ (PO₄)₂, Tavorite structured compounds such as Mg₀.₅VPO₄F, pyrophosphates such as TiP₂O₇ and VP₂O₇, and fluorides such as FeF₃.

According to conventional practice, the positive electrode may also contain an electronically conductive additive, such as carbon black, Super P, Super C65, Ensaco black, Ketjen black, acetylene black, synthetic graphite such as Timrex SFG-6, Timrex SFG-15, Timrex SFG-44, Timrex KS-6, Timrex KS-15, Timrex KS-44, natural flake graphite, carbon nanotubes, fullerenes, hard carbon, and mesocarbon microbeads.

Additionally, the positive electrode may further comprise a polymer binder. Non-limiting examples of polymer binders include poly-vinylidene fluoride (PVdF), poly(vinylidene fluoride-co-hexafluoropropene) (PVdF-HFP), Polytetrafluoroethylene (PTFE), Kynar Flex 2801, Kynar Powerflex LBG, and Kynar HSV 900, and Teflon. Polyvinylidene fluoride (PVdF) is a preferred binder.

Solvents suitable in the Mg battery may be any aprotic solvent which is compatible with magnesium and the other components of the battery, including the magnesium salt of formula (I). Conventional solvents selected from the group consisting of tetrahydrofuran. 2-methyl tetrahydrofuran, dimethoxyethane, glyme, monoglyme, dimethyl glycol, dimethyl ether, diethyl ether, ethyl glyme, diglyme, proglyme, ethyl diglyme, triglyme, butyl diglyme, tetraglyme, polyglyme, higlyme, and combinations thereof may be included in the claimed Mg battery.

Halide containing solvents and halide salts are excluded from the Mg battery as described above.

The Mg battery according to the invention may be constructed by methods which are conventionally known and may be a button or coin cell battery consisting of a stack of negative electrodes, porous polypropylene or glass fiber separators, and positive electrode disks in a can base onto which a can lid is crimped. Alternatively, the Mg battery may be a stacked cell battery. In other embodiments, the Mg battery may be a prismatic, or pouch, cell consisting of one or more stacks of negative electrode, porous polypropylene or glass fiber separator, and positive electrode sandwiched between current collectors, as described above. The stack(s) may be folded within a polymer coated aluminum foil pouch, vacuum and heat dried, filled with electrolyte, and vacuum and heat sealed. In other embodiments, the Mg battery may be a prismatic, or pouch, bi-cell consisting of one or more stacks of a positive electrode which is coated with active material on both sides and wrapped in porous polypropylene or glass fiber separator, and a negative electrode folded around the positive electrode. The stack(s) are folded within a polymer coated aluminum foil pouch, dried under heat and/or vacuum, filled with electrolyte, and vacuum and heat sealed. In some embodiments of the prismatic or pouch cells described herein, an additional tab composed of a metal foil or carbonaceous material may be affixed to the current collector by laser or ultrasonic welding, adhesive, or mechanical contact, in order to connect the electrodes to the device outside the packaging. In other embodiments, the Mg battery disclosed herein is a wound or cylindrical cell consisting of wound layers of one or more stacks of a positive electrode which is coated with active material on one or both sides, sandwiched between layers of porous polypropylene or glass fiber separator, and a negative electrode. The stack(s) are wound into cylindrical roll, inserted into the can, dried under heat and/or vacuum, filled with electrolyte, and vacuum and welded shut. In some embodiments of the cylindrical cells described herein, an additional tab composed of a metal foil or carbonaceous material may be affixed to the current collector by laser or ultrasonic welding, adhesive, or mechanical contact, in order to connect the electrodes to the device outside the packaging.

The stainless steel component, including the current collector may be constructed of any of the conventionally known stainless types, including 302, 304, 305, 316 and 384.

Having generally described this invention, a further understanding can be obtained by reference to certain specific examples which are provided herein for purposes of illustration only and are not intended to be limiting unless otherwise specified. Skilled artisans will recognize the utility of the devices of the present invention as a battery as well as the general utility of the electrolyte system described herein.

EXAMPLES

Figure 1:
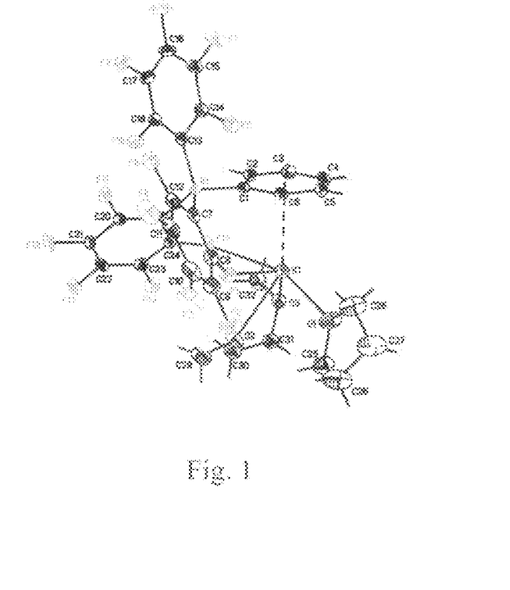
FIG. 1 shows an ORTEP plot (25% thermal probability ellipsoids) of $(PhB(C_6F_5)_3)K$ prepared in the Example. Hydrogen atoms are omitted for clarity.
Figure 2:
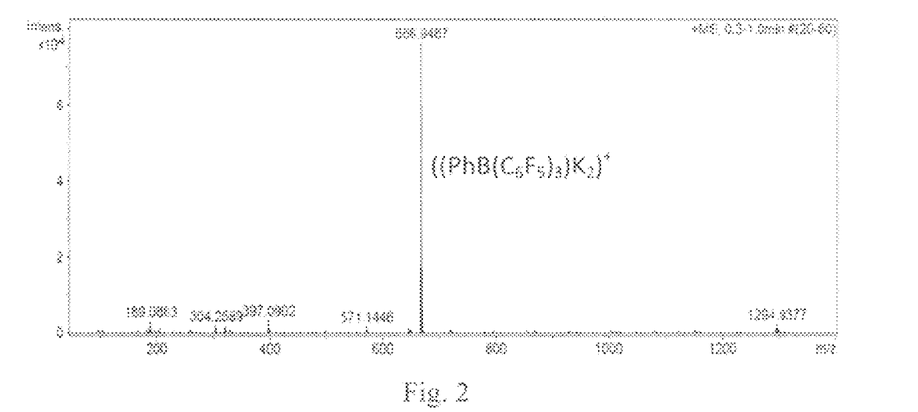
FIG. 2 shows the mass spectrum of the potassium salt $((PhB(C_6F_5)_3)K_2)^+$ prepared in the Example.
Figure 3:
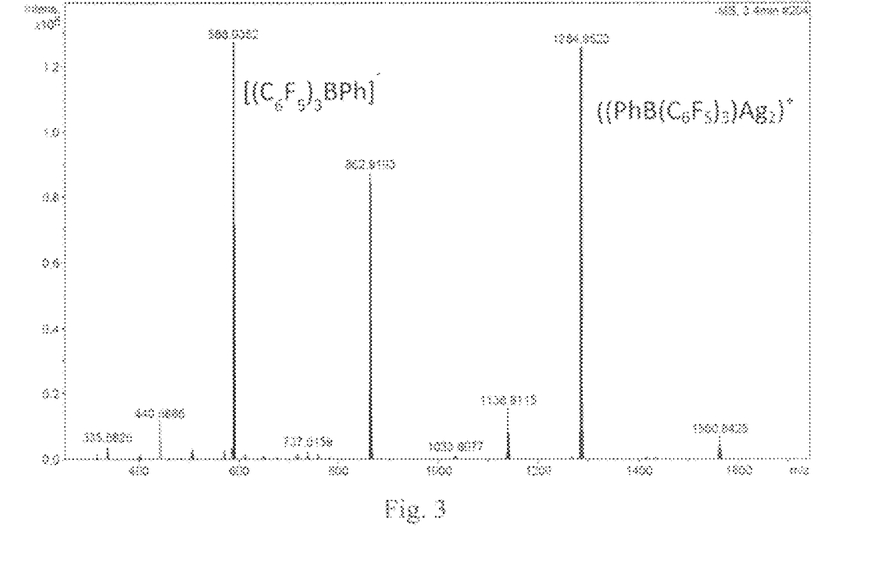
FIG. 3 shows the mass spectrum of the silver salt $((PhB(C_6F_5)_3)Ag_2)^+$ prepared in the Example.

Preparation of $((C_6H_5)B(C_6F_5)_3)K$ 2 g of the Lewis acid $B(C_6F_5)_3$ were dissolved in 10 ml of THF. 5.5714 ml of PhMgCl in THF (2.0M solution) was added rapidly. The reaction was allowed to stir for 3 days after which the in situ generated electrolyte of gen3 was added to 100 ml of an aqueous solution of 1M of $K_2CO_3$ and $KHCO_3$. The reaction was allowed to stir for 4 hours after which the potassium salt was extracted with ether. The ether extract was dried over anhydrous magnesium sulfate and put under high vacuum overnight. The yield of the potassium salt was 2.5 g. The NMR of the potassium salt is in the appendix. It is impossible, based on $^{19}F$ and $^1H$ NMR to distinguish between gen3 electrolyte and $(PhB(C_6F_5)_3)K$. (The structure of the potassium salt can only be confirmed by mass spectrometry where the isotope pattern and exact mass of 666.9487 is consistent with $((PhB(C_6F_5)_3)K_2)^+$.) X-ray structure in FIG. 1. Crystal data for $C_{32}H_{23}BF_{15}KO_3$; $M_r$=790.41; Monoclinic; space group $P2_1/c$; a=19.5325(15) Å; b=10.0374(7) Å; c=18.1523(14) Å; α=90°; β=117.094(3)°; γ=90°; V=3168.3(4) Å$^3$; Z=4; T=120(2) K; λ(Mo—Kα)=0.71073 Å; μ(Mo—Kα)=0.292 mm$^{-1}$; $d_{calc}$=1.657 g·cm$^{-3}$; 66367 reflections collected; 7938 unique ($R_{int}$=0.0403); giving $R_1$=0.0485, $wR_2$=0.1234 for 6173 data with [I>2σ(I)] and $R_1$=0.0667, $wR_2$=0.1364 for all 7938 data. Residual electron density (e$^-$·Å$^{-3}$) max/min: 2.498/−0.755. An arbitrary sphere of data were collected on a colorless block-like crystal, having approximate dimensions of 0.128×0.119×0.106 mm, on a Bruker Kappa X8-APEX-II diffractometer using a combination of ω- and φ-scans of 0.5° [1]. Data were corrected for absorption and polarization effects and analyzed for space group determination. The structure was solved by intrinsic phasing methods and expanded routinely [2]. The model was refined by full-matrix least-squares analysis of F$^2$ against all reflections. All non-hydrogen atoms were refined with anisotropic thermal displacement parameters. Unless otherwise noted, hydrogen atoms were included in calculated positions. Thermal parameters for the hydrogens were tied to the isotropic thermal parameter of the atom to which they are bonded (1.5× for methyl, 1.2× for all others).

Preparation of $((C_6H_5)B(C_6F_3)_3)Ag$

The silver salt was prepared based upon the reference Buschmann et al. (Chem. Eur. J 1998, 4, no 9 1731). In summary, the potassium salt is converted to the silver salt by reacting with silver nitrate in acetonitrile. During the reaction ether is added to help precipitate the potassium nitrate. The precipitate is removed by filtering and the silver salt is obtained by evaporating the acetonitrile. Unfortunately the silver salt is very reactive and decomposes rapidly in light. The conversion to the silver salt was confirmed by mass spectroscopy where the isotope pattern and the exact mass of 1284.9523 is consistent with the cation $((C_6H_5)B(C_6F_5)_3)Ag_2)^+$.

Preparation of $(C_6H_5)B(C_6F_5)_3)_2Mg$

The magnesium salt was obtained by the reaction of the silver salt with half an equivalent of anhydrous magnesium bromide in THF. Over the course of the reaction, the silver bromide precipitated and this precipitation was indicative of the conversion. Crystals of the product were obtained by layering the THF solution containing the magnesium salt with hexane.

Figure 4:
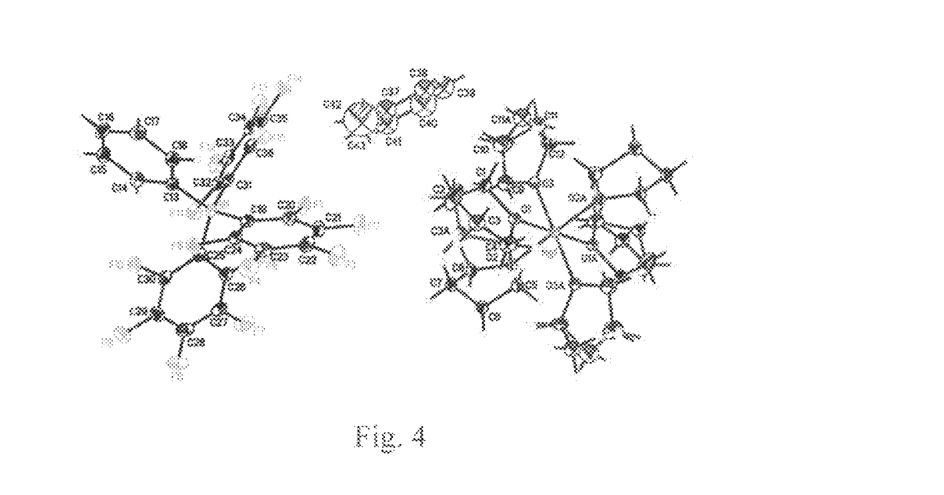
FIG. 4 shows an ORTEP plot (25% thermal probability ellipsoids) of $(PhB(C_6F_5)_3)_2Mg$ prepared in the Example. Hydrogen atoms are omitted for clarity.

$((C_6H_5)B(C_6F_5)_3)_2Mg$ was crystallized as colorless tablet-like crystals from a toluene solution. An ORTEP plot (see FIG. 4) showed that there are one molecule of the Mg cation, two molecules of the tris-perfluorophenyl, phenyl borate anion and one molecule of toluene in the unit cell of the primitive, centro symmetric, triclinic space group P-1. The magnesium is coordinated in an octahedral fashion by six molecules of THF. It is located on an inversion center at the origin of the unit cell. The asymmetric unit only shows three molecules of THF and half an Mg atom. Two of the three independent THF molecules exhibit positional disorder in one of the carbon atoms in the THF moiety. These carbon atoms were modeled over two sites and the occupancies of the major and minor components in each disorder were refined summed to unity, yielding an approximately 0.66: 0.34 and 0.75:0.25 ratio for the two sites (see appendix for X-ray data). The bond distances and angles within the molecules are unexceptional.

$((C_6H_5)B(C_6F_5)_3)_2Mg$ may also be obtained from the potassium salt directly in Glyme by reaction with MgBr2

X-ray Structure of $((C_6H_5)B(C_6F_5)_2Mg$

Crystal data for $C_{39.50}H_{33}BF_{15}Mg_{0.50}O_3$; $M_r$=863.62; Triclinic; space group P-1; a=12.0179(12) Å; b=12.5648(13) Å; c=13.7173(14) Å; α=102.5881(16)°; β=90.2857(17)°; γ=115.1883(15)°; V=1818.1(3) Å$^3$; Z=2; T=120(2) K; λ(Mo—Kα)=0.71073 Å; μ(Mo—Kα)=0.158 mm$^{-1}$; $d_{calc}$=1.578 g·cm$^{-3}$; 42372 reflections collected; 7303 unique ($R_{int}$=0.0479); giving $R_1$=0.0514, $wR_2$=0.1098 for 5451 data with [I>2σ(I)] and $R_1$=0.0757, $wR_2$=0.1209 for all 7303 data. Residual electron density (e$^-$·Å$^{-3}$) max/min: 1.313/−0.576. An arbitrary sphere of data were collected on a colorless tablet-like crystal, having approximate dimensions of 0.146×0.103×0.057 mm, on a Bruker APEX-II diffractometer using a combination of ω- and φ-scans of 0.5° [1]. Data were corrected for absorption and polarization effects and analyzed for space group determination. The structure was solved by Patterson methods and expanded routinely [2]. The model was refined by full-matrix least-squares analysis of F$^2$ against all reflections. All non-hydrogen atoms were refined with anisotropic thermal displacement parameters. Unless otherwise noted, hydrogen atoms were included in calculated positions. Thermal parameters for the hydrogens were tied to the isotropic thermal parameter of the atom to which they are bonded (1.5× for methyl, 1.2× for all others).

The invention claimed is:

1. A method to prepare a nonaqueous magnesium electrolyte, the nonaqueous magnesium electrolyte comprising:
a nonaqueous solvent comprising an ether oxygen; and
a magnesium salt of formula (I):

$$[A]_2Mg(Solvent))_y \qquad (I)$$

wherein
the electrolyte does not comprise chloride ions,
Solvent is the nonaqueous solvent comprising the ether oxygen and y is an integer of 2 to 6, and
A is at least one of a water stable borate anion or a water stable carborate anion;
the method comprising:
reacting a Grignard reagent of formula RMgCl with i) a borane of formula $BR_3$ wherein each R is independently selected from the group consisting of an alkyl group of 1-6 carbon atoms, optionally substituted with F, an aryl group optionally substituted with F, and an alkylphenyl group optionally substituted with F; or ii) a carborane of formula $C_2B_{10}H_{12}$ in tetrahydrofuran to obtain a magnesium salt of formula:

$$[Mg_2(\mu\text{-}Cl)_3 \cdot 6THF]A$$

wherein A is i) a borate anion of formula $BR_4^-$ (II) wherein each R is independently selected from the group consisting of an alkyl group of 1-6 carbon atoms, optionally substituted with F, an aryl group optionally substituted with F, and an alkylphenyl group optionally substituted with F; or ii) a carborate anion of formula $C_2B_{10}H_{11}^-$ (III);
forming a $M^+$ salt of the anion A in an aqueous medium according to:

$$3[Mg_2(\mu\text{-}Cl)_3 \cdot 6THF]A + M_2CO_3/MHCO_3(aq) \rightarrow 3MA + [Mg_2(\mu\text{-}Cl)_3 \cdot 6THF]_2(CO_3) + [Mg_2(\mu\text{-}Cl)_3 \cdot 6THF](HCO_3):$$

extracting the MA salt from the aqueous medium;
isolating the free MA salt from the extract; and
ion exchange of $Mg^{2+}$ for the metal ion $M^+$ of the MA salt to obtain the Mg salt of formula (I),
wherein the metal ion ($M^+$) is at least one selected from the group consisting of $Li^+$, $Na^+$, $K^+$ $Rb^+$, $Cs^+$ and $Ag^+$.

2. The method according to claim 1, wherein $M^+$ is $Ag^+$.

3. The method according to claim 1, wherein $M^+$ is $K^+$.

4. The method according to claim 3, wherein
the KA salt is extracted in ether; and
the KA salt is isolated by removing the ether under vacuum.

5. The method according to claim 4, further comprising:
forming a $Ag^+$ salt of the anion A according to the exchange (b) in a medium wherein $KNO_3$ is insoluble:

$$KA + AgNO_3 \rightarrow AgA + KNO_3(s) \qquad (b);$$

and
removing the precipitated $KNO_3(s)$ from the solution of the AgA salt.

6. The method according to claim 1, wherein the borate anion of formula $BR_4^-$ (II) is an anion of formula (IV):

$$[BPh_4]^- \qquad (IV)$$

wherein each Ph group is independently selected from the group consisting of an aryl group optionally substituted with F, and an alkyphenyl group optionally substituted with F.

7. The method according to claim 6, wherein the borate anion of formula (IV) is the anion of formula (V):

$$[(C_6F_5)_3B(C_6H_5)]^- \qquad (V).$$

8. The method according to claim 6, wherein the borate anion of formula (IV) is the anion of formula (VI):

$$[(Mes)_3B(C_6H_5)]^- \qquad (VI)$$

wherein Mes is a 3,5-dimethylphenyl group.

9. The method according to claim 1 wherein A is the carborate anion of formula (III):

$$(C_2B_{10}H_{11})^- \qquad (III)$$

wherein the carborate anion is an anion of an ortho-carborane, an anion of a meta-carborane or an anion of a para-carborane.

10. The method according to claim 1, wherein the nonaqueous solvent comprising an ether oxygen is at least one of tetrahydrofuran (THF), dimethoxyethane (DME) and diethylene glycol dimethyl ether (diglyme) (DGM).

11. A method to prepare a magnesium electrolyte, comprising:
tetrahydrofuran; and
a salt of formula (VII):

$$[(C_6F_5)_3B(C_6H_5)]_2Mg(THF)_6 \qquad (VII)$$

wherein THF is a tetrahydrofuran molecule,
the method comprising:
reacting a Grignard reagent of formula $C_6H_5MgCl$ with a borane of formula $B(C_6F_5)_3$ in tetrahydrofuran to obtain a magnesium salt of formula:

$$[Mg_2(\mu\text{-}Cl)_3 \cdot 6THF][(C_6H_5)B(C_6F_5)_3]$$

forming a $K^+$ salt of the anion $(C_6H_5)B(C_6F_5)_3$ in an aqueous medium according to:

$$3[Mg_2(\mu\text{-}Cl)_3 \cdot 6THF][(C_6H_5)B(C_6F_5)_3] + K_2CO_3/KHCO_3(aq) \rightarrow 3K[(C_6H_5)B(C_6F_5)_3] + [Mg_2(\mu\text{-}Cl)_3 \cdot 6THF]_2(CO_3) + [Mg_2(\mu\text{-}Cl)_3 \cdot 6THF](HCO_3):$$

forming a $Ag^+$ salt of the anion $(C_6H_5)B(C_6F_5)_3^-$ according to the exchange (b) in a medium wherein $KNO_3$ is insoluble:

$$K[(C_6H_5)B(C_6F_5)_3] + AgNO_3 \rightarrow Ag[(C_6H_5)B(C_6F_5)_3] + KNO_3(s) \qquad (b);$$

and
removing the precipitated $KNO_3(s)$ from the solution of the $Ag[(C_6H_5)B(C_6F_5)_3]$ salt
ion exchange of Mg for Ag in THF according to the equation:

$$2((C_6H_5)B(C_6F_5)_3)Ag + MgBr_2 \rightarrow ((C_6H_5)B(C_6F_5)_3)_2Mg(THF)_6 + 2AgBr$$

and removal of the AgBr from the magnesium electrolyte,
wherein the magnesium electrolyte does not comprise a chloride ion.

12. A method to prepare a magnesium electrolyte, comprising:
tetrahydrofuran; and
a salt of formula (VIII):

$$[(Mes)_3B(C_6H_5)_3]_2Mg(THF)_6 \qquad (VIII)$$

wherein
THF is a tetrahydrofuran molecule,
and
Mes is a 3,5-dimethylphenyl group,
the method comprising:
reacting a Grignard reagent of formula $C_6H_5MgCl$ with a borane of formula
$B(Mes)_3$ in tetrahydrofuran to obtain a magnesium salt of formula:

$$[Mg_2(\mu\text{-}Cl)_3 6THF][(C_6H_5)B(Mes)_3]$$

forming a K⁺ salt of the anion (C₆H₅)B(Mes)₃ in an aqueous medium according to:

forming a Ag⁺ salt of the anion (C₆H₅)B(Mes)₃⁻ according to the exchange (b) in a medium wherein KNO₃ is insoluble:

K((C₆H₅)B(Mes)₃+AgNO₃ →Ag[(C₆H₅)B(C₆F₅)₃]+ KNO₃(s)   (b);

and
removing the precipitated KNO₃(s) from the solution of the Ag[(C₆H₅)B(Mes)₃] salt
ion exchange of Mg for Ag in THF according to the formula:

and removal of the AgBr from the magnesium electrolyte,
wherein the magnesium electrolyte does not comprise a chloride ion.

13. A magnesium electrolyte obtained according to the method of claim 1, comprising:
a nonaqueous solvent comprising an ether oxygen; and
a salt of formula (I):

[A]₂Mg(Solvent)ᵧ   (I)

wherein
Solvent is the nonaqueous solvent comprising the ether oxygen and is at least one selected from the group consisting of tetrahydrofuran, 2-methyl tetrahydrofuran, dimethoxyethane, glyme, monoglyme, dimethyl glycol, ethylene glycol dimethyl ether, diethyl ether, ethyl glyme, diglyme, proglyme, ethyl diglyme, triglyme, butyl diglyme, tetraglyme, polyglyme and higlyme,
y is an integer of 2 to 6,
A is a water stable borate anion or a water stable carborate anion selected from the group of anions consisting of:

(BR₄)⁻   (II)

wherein the R groups are each independently selected from the group consisting of an alkyl group of 1-6 carbon atoms, optionally substituted with F, an aryl group optionally substituted with F, and an alkylphenyl group optionally substituted with F and (C₂B₁₀H₁₁)⁻   (III)

and
the magnesium electrolyte is free of chlorides.

14. A magnesium battery, comprising:
a negative electrode comprising magnesium;
a positive electrode ; and
the magnesium electrolyte according to claim 13.

15. The magnesium battery, according to claim 14, wherein the negative electrode is magnesium.

16. The magnesium battery, according to claim 14, wherein
the positive electrode active material comprises at least one component selected from the group consisting of Sulfur, graphitic carbon, carbon fiber, glassy carbon, pyrolitic carbon, amorphous carbon, Mo₆S₈, MnO₂, CuS, Cu₂S, Ag₂S, CrS₂, VOPO₄, TiS₂, V₂O₅, MgVO₃, MoS₂, MgV₂O₅, MoO₃, CuCr₂S₄, MgCr₂S₄, MgMn₂O₄, Mg₂MnO₄, MgFe₂(PO4)₃, MgV₂(PO₄)₃, MgMnSiO₄, MgFe₂(PO₄)₂, Mg₀.₅VPO₄F, TiP₂O₇, VP₂O₇ and FeF₃.

17. The magnesium battery, according to claim 14, wherein
A is the borate anion of formula (II):

(BR₄)⁻   (II)

wherein the R groups are each independently selected from the group consisting of an alkyl group of 1-6 carbon atoms, optionally substituted with F, an aryl group optionally substituted with F, and an alkylphenyl group optionally substituted with F.

18. The magnesium battery, according to claim 17, wherein
the borate anion of formula (II) is an anion of formula (IV):

[B(C₆H₅)₄]⁻   (IV)

wherein each Ph group is independently selected from the group consisting of an aryl group optionally substituted with F, and an alkyphenyl group optionally substituted with F.

19. The magnesium battery, according to claim 17, wherein
the borate anion of formula (II) is the anion of formula (V):

[((C₆F₅)₃B(C₆H₅)]⁻   (V).

20. The magnesium battery, according to claim 17, wherein
the borate anion of formula (II) is the anion of formula (VI):

[(Mes)₃B(C₆H₅)]⁻   (VI)

wherein Mes is a 3,5-dimethylphenyl group.

21. The magnesium battery according to claim 14, wherein A is the carborate anion of formula (III):

(C₂B₁₀H₁₁)⁻   (III)

wherein the carborate is an anion of an ortho-carborane, meta-carborane or para-carborane.

* * * * *